United States Patent [19]

Murata

[11] 4,315,745
[45] Feb. 16, 1982

[54] DENTAL ELEVATOR

[76] Inventor: Seitaro Murata, 32-4, Matsuyama 1-chome, Naha-shi, Okinawa-ken, Japan

[21] Appl. No.: 207,573

[22] Filed: Nov. 17, 1980

[30] Foreign Application Priority Data

Nov. 20, 1979 [JP] Japan .............. 54-161477[U]

[51] Int. Cl.$^3$ ............................... A61C 3/00
[52] U.S. Cl. .................... 433/141; 433/152
[58] Field of Search ............ 433/141, 145, 152

[56] References Cited

U.S. PATENT DOCUMENTS 1,606,686  11/1926  Barry ...................... 433/141

FOREIGN PATENT DOCUMENTS 140222  3/1953  Sweden ...................... 433/141

OTHER PUBLICATIONS

Dental Industry New, Jun. 1979, New Products.

Primary Examiner—Robert Peshock
Attorney, Agent, or Firm—Jordan and Hamburg

[57] ABSTRACT

Dental elevator comprising a holder portion (3), a stem portion (5) and a beak portion (7), the improvement is characterized in that the beak portion has an extremity (a) thereof formed in a shape selected from a group consisting of a U-shape, a V-shape and a zigzag or serrated shape. Due to such construction, the dental elevator can easily extract a tooth efficiently utilizing a lever action and a wedge action.

4 Claims, 10 Drawing Figures

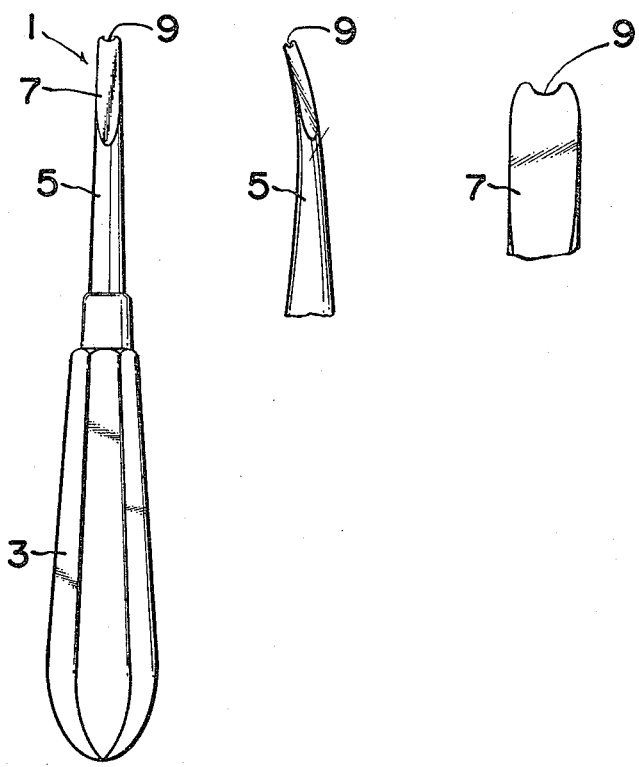
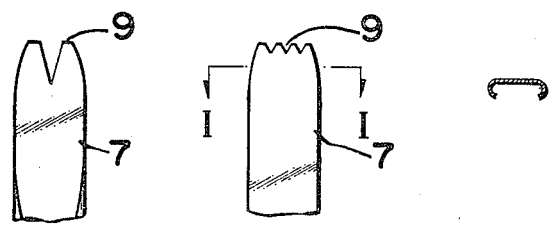

DENTAL ELEVATOR

BACKGROUND OF INVENTION

This invention relates to a dental elevator employed for tooth extraction.

The conventional dental elevators which are commercially available comprise a holder portion, a stem portion and a beak portion. These dental elevators which are popularly called T-shape (No. 1–No. 8) or #6 are generally classified into the following groups depending on the shape of the respective beak portions, namely (a) a straight beak, (b) warped beak, (c) bayonet beak, and (d) bent beak.

The width of the beak portion at the extremity thereof varies from 2 mm to 4 mm in the order of 0.5 mm and the shape of the extremity is usually either semi-circular or convex.

In a tooth-extracting operation using the above-mentioned dental elevator, as shown in FIG. 1, the beak portion of the elevator (11) is urgingly inserted in the periodontal cavity (23) and then the tooth is dislocated by the wedge action and the lever action of the elevator (11), thereby extracting the tooth. In this operation, however, as shown in the drawing, since the extremity (19) of the beak portion (17) which is attached to the holder portion (13) is provided with a semi-circular or gradually protruded convex shape, even when the dental root is urgingly lifted by the lever action using the periphery (21) of alveolar bone which is located opposite to the surface of the dental root (25) as the fulcrum of the lever, the beak extremity (19) cannot firmly engage the tooth. Therefore, the dentist may have to repeat the above lifting operations many times before completion of the tooth extraction.

Furthermore, since the beak portion of the conventional dental elevator slips during the operation, there is a good chance that the elevator injures the portions of the mouth surrounding the tooth to be extracted. It is considered that although the wedge action forms one of the essential functions in extracting the tooth, such conventional elevator cannot effect the above function efficiently due to the convex or round semi-circular extremity (19) of the beak portion.

The operation with these dental elevators is eventually very cumbersome and results in discomfort to the doctor as well as the patient.

It is an object of the present invention to provide a novel dental elevator which can firmly engage with the dental root without incurring slipping thereof, whereby the tooth can be readily extracted utilizing the wedge and lever actions efficiently.

BRIEF DESCRIPTION OF THE DISCLOSURE

FIG. 1 is an explanatory view showing a conventional dental elevator dislocating and extracting a tooth by urgingly inserting thereof into the peridontal cavity along the surface of the dental root, FIG. 2 is an explanatory view showing a dental elevator according to this invention dislocating and extracting a tooth by urgingly inserting thereof into the peridontal cavity along the surface of the dental root, FIG. 3 is a front view of a conventional dental elevator, FIG. 3a is a partial front view of the above elevator but in a slightly angularily shifted position relative to the position in FIG. 3, FIG. 4 is a front view of the dental elevator of this invention, FIG. 4a is a partial front view of the above elevator but in a slightly angularily shifted position relative to the position in FIG. 4, FIG. 5 is an enlarged front view of the beak portion of the above elevator of FIG. 4, FIG. 6 is an enlarged front view of the beak portion of the elevator of another embodiment of this invention, FIG. 7 is an enlarged front view of the beak portion of the elevator of still another embodiment of this invention, and FIG. 8 is a transverse cross sectional view of the above elevator taken along the line I—I of FIG. 7.

DETAILED DESCRIPTION OF THE DISCLOSURE

Figure 1:
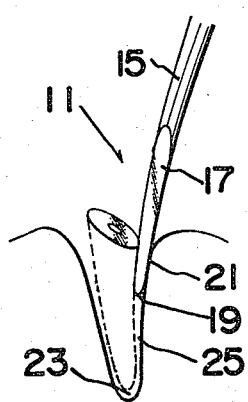
Figure 2:
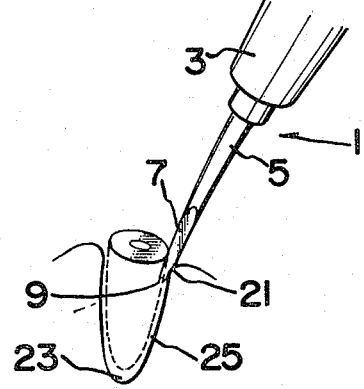
Figure 3:
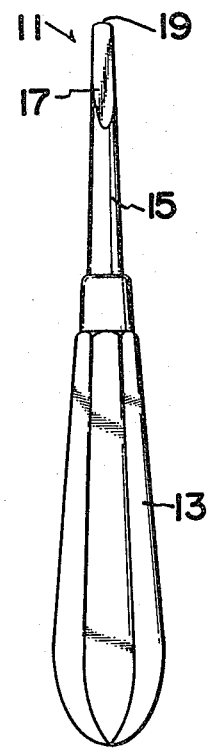
Figure 3A:

The dental elevator of this invention is described in detail hereinafter in conjunction with attached drawings.

In FIG. 4 to FIG. 5, a dental elevator (1) according to the first embodiment of this invention is provided with a straight beak portion (7) (an orthodox type). The beak portion (7) defines the distal end of an elongated stem portion (5), while the stem portion (5) is provided with a holder portion (3) at the proximal end thereof. In this embodiment, as shown in FIG. 5, the beak portion (7) has the extremity (9) thereof formed with a U-shaped concave configuration. Due to such construction, when the elevator (1) is urgingly inserted in a peridontal cavity (23), since the surface of a dental root (25) has some degree of resiliency, the beak extremity (9) can snugly fit on the surface of the dental root (25) and thereby can firmly hold and grasp the dental root (25).

This implies that the beak portion (9) can assure sufficient contact area with the periphery of the alveolar bone (21) which works as the fulcrum of the lever action. Therefore, the dental elevator (1) can conduct a stable lever action in operation and can extremely easily extract the tooth.

FIG. 6 shows another embodiment of the dental elevator of this invention, wherein the dental elevator is characterized in that the beak extremity (9) of the beak portion (7) is formed with a V-shaped concave configuration.

In FIG. 7 still another embodiment of the dental elevator of this invention is shown, wherein the beak extremity (9) of the beak portion (7) is formed in a serrated or zigzag shape. Such beak extremity (9) can provide almost the same functions as those of the dental elevator (1) of FIG. 4.

The most preferable embodiment of the dental elevator of this invention is that the beak extremity (9) of the beak portion (7) has a cross section of a flattened chisel.

The dental elevator of the last embodiment shown in FIG. 7 well meets this requirement and, as shown in FIG. 8, the beak extremity (9) has a approximately-flattened-chisel cross section. In a tooth extracting operation by the above elevator (1), when the flattened-chisel-like beak extremity (9) is urgingly inserted in the peridontal cavity (21), such beak extremity (9) can intrude between the dental root and the alveolar bone, thus can easily dislocate the tooth by fully making use of the wedge action.

Although, the present invention is described in view of the dental elevator having a straight beak portion, it is needless to say that the present invention includes other dental elevators having warped-type, bayonet-type, and bent-type beak portions within the scope of protection.

The choice of either U-shape or V-shape as the preferred shape of the beak extremity (9) depends usually on the width of the beak extremity (9).

As has been described heretofore, since the dental elevator of this invention is provided with one of the U-shaped concave beak extremity, V-shaped concave beak extremity or zigzag shaped beak extremity, such elevator can firmly engage the dental root promoting the effects of wedge and lever actions, whereby the tooth can be extremely easily extracted.

What we claim is:

1. Dental elevator comprising a holder portion, a stem portion and a beak portion,
   the improvement is characterized in that
   (i) said holder portion, said stem portion and said beak portion being constructed as a substantially straight and integral elongated bar,
   (ii) said beak portion having one longitudinal side flattened like a chisel surface and the other longitudinal side rounded, said flattened side extending to the terminating end of said beak portion,
   (iii) said beak portion having a thickness and a width narrowed gradually toward said terminating end of said beak portion, and
   (iv) said beak portion being with a V-shaped notch opening onto said terminating end with the apex of the V being spaced from said terminating end and the legs of the V ending at said terminating end, whereby said notch is engageable with the root of a tooth being extracted to prevent slipping of the dental elevator on said root during extraction.

2. Dental elevator according to claim 3, wherein said extremity of said beak portion has a transverse cross section of a flattened chisel.

3. Dental elevator comprising a holder portion, a stem portion and a beak portion,
   the improvement is characterized in that
   (i) said holder portion, said stem portion and said beak portion being constructed as a substantially straight and integral elongated bar,
   (ii) said beak portion having one longitudinal side flattened like a chisel surface and the other longitudinal side rounded, said flattened side extending to the terminating end of said beak portion,
   (iii) said beak portion having a thickness and a width narrowed gradually toward said terminating end of said beak portion, and
   (iv) said beak portion being with a U-shaped notch opening onto said terminating end with the base of the U being spaced from said terminating end and the legs of the U ending at said terminating end, whereby said notch is engageable with the root of a tooth being extracted to prevent slipping of the dental elevator on said root during extraction.

4. Dental elevator according to claims 1 or 3 wherein a plurality of said notches are provided on said beak portion.

* * * * *